US011195620B2

(12) United States Patent
Wang et al.

(10) Patent No.: US 11,195,620 B2
(45) Date of Patent: Dec. 7, 2021

(54) PROGRESS EVALUATION OF A DIAGNOSIS PROCESS

(71) Applicant: International Business Machines Corporation, Armonk, NY (US)

(72) Inventors: Jian Wang, Beijing (CN); Yi Peng Yu, Beijing (CN); Shao Chun Li, Beijing (CN); Ya Bin Dang, Beijing (CN); Hao Chen, Beijing (CN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 181 days.

(21) Appl. No.: 16/240,437

(22) Filed: Jan. 4, 2019

(65) Prior Publication Data
US 2020/0219618 A1     Jul. 9, 2020

(51) Int. Cl.
| G16H 50/20 | (2018.01) |
| G06N 5/00 | (2006.01) |
| G06N 5/02 | (2006.01) |
| G06F 40/40 | (2020.01) |

(52) U.S. Cl.
CPC .............. *G16H 50/20* (2018.01); *G06F 40/40* (2020.01); *G06N 5/003* (2013.01); *G06N 5/02* (2013.01)

(58) Field of Classification Search
CPC ....... G06N 20/00; G06F 16/337; G06F 40/56; G06F 19/00; G06F 19/3418; G06F 16/24542; G06F 17/18; G06F 40/20; G06F 40/40; G16H 10/20; G16H 10/60;
(Continued)

(56) References Cited

U.S. PATENT DOCUMENTS

| 7,137,389 B2 * | 11/2006 | Berthon-Jones ...... A61M 16/06 128/204.18 |
| 7,344,496 B2 | 3/2008 | Iliff |

(Continued)

FOREIGN PATENT DOCUMENTS

| EP | 3032472 A1 | 6/2016 |
| JP | 2018172167 A * | 11/2018 |

OTHER PUBLICATIONS

Afonso, Anna M; Ebell, Mark H; Tarleton, Rick L. A systematic review of high quality diagnostic tests for Chagas disease. PLoS Neglected Tropical Diseases6.11: NA. Public Library of Science. (Nov. 2012) (Year: 2012).*

(Continued)

*Primary Examiner* — Linh Giang Le
(74) *Attorney, Agent, or Firm* — Amin, Turocy & Watson, LLP (57) ABSTRACT

Computer-implemented methods, computer program products, and system facilitating evaluation of a progress of a diagnosis process are provided. The computer-implemented method comprises: obtaining, by a device operatively coupled to one or more processing units, a list of symptom(s); retrieving, by the device, a sub-graph associated with the list of symptom(s) from a knowledge graph; extracting, by the device, a list of feature(s) from the retrieved sub-graph; estimating, by the device, an average number of inquiries based on the extracted list of feature(s); and calculating, by the device, the progress of the diagnosis process based on the estimated average number of inquiries.

20 Claims, 6 Drawing Sheets

(58) Field of Classification Search
CPC ........ G16H 40/20; G16H 50/20; G16H 50/30; G16H 70/60
USPC .......................................................... 705/2
See application file for complete search history.

(56) References Cited

U.S. PATENT DOCUMENTS

| | | | |
|---|---|---|---|
| 2002/0040183 A1* | 4/2002 | Iliff ........................ | G16H 70/60 600/300 |
| 2012/0084092 A1* | 4/2012 | Kozuch .................. | G16H 50/20 705/2 |
| 2012/0185275 A1* | 7/2012 | Loghmani .............. | G16H 10/60 705/3 |
| 2014/0279746 A1* | 9/2014 | De Bruin ............... | G16H 10/40 706/12 |
| 2017/0249434 A1* | 8/2017 | Brunner .............. | G06F 19/3418 |
| 2018/0011979 A1 | 1/2018 | Zhong et al. | |

OTHER PUBLICATIONS

Jiang et al., "Learning and inference in knowledge-based probabilistic model for medical diagnosis," Knowledge-Based Systems, Dec. 2017, pp. 58-68, vol. 138, 32 pages.

Goodwin et al., "Medical Question Answering for Clinical Decision Support," Proceedings of the ACM International Conference on Information & Knowledge Management, Oct. 2016, pp. 297-306, ACM, 22 pages.

Rotmensch et al., "Learning a Health Knowledge Graph from Electronic Medical Records," Scientific Reports, 2017, vol. 7, Article No. 5994, 31 pages.

"Information gain in decision trees," Wikipedia, 4 pages. Retrieved on Dec. 10, 2018. https://en.wikipedia.org/wiki/Information_gain_in_decision_trees.

Mell et al., "The NIST Definition of Cloud Computing," National Institute of Standards and Technology, Sep. 2011, Special Publication 800-145, U.S Department of Commerce, 7 pages.

* cited by examiner

PROGRESS EVALUATION OF A DIAGNOSIS PROCESS

BACKGROUND

One or more embodiments relates to improved data processing, and more specifically, to progress evaluation of a knowledge graph-based diagnosis process.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

Artificial intelligence (AI) makes it possible for machines to learn from experience, adjust to new inputs and perform human-like tasks. Most AI examples today rely heavily on deep learning and natural language processing. Using these technologies, computers can be trained to accomplish specific tasks by processing large amounts of data and recognizing patterns in the data. With the development of AI technologies, more and more industries are beginning to apply AI to help to solve industry-specific problems.

In one illustrative embodiment of the present invention, there is provided a computer implemented method. The method comprises: obtaining, by a device operatively coupled to one or more processing units, a list of symptom(s); retrieving, by the device, a sub-graph associated with the list of symptom(s) from a knowledge graph; extracting, by the device, a list of feature(s) from the retrieved sub-graph; estimating, by the device, an average number of inquiries based on the extracted list of feature(s); and calculating, by the device, the progress of the diagnosis process based on the estimated average number of inquiries.

Computer program products and computer systems are also provided.

These and other features and advantages of the present invention will be described in, or will become apparent to those of ordinary skill in the art in view of, the following detailed description of the example embodiments of the present invention.

BRIEF DESCRIPTION OF THE DRAWINGS

Through the more detailed description of some embodiments of the present disclosure in the accompanying drawings, the above and other objects, features and advantages of the present disclosure will become more apparent, wherein the same reference generally refers to the same components in the embodiments of the present disclosure.

DETAILED DESCRIPTION

Some embodiments will be described in more detail with reference to the accompanying drawings, in which the embodiments of the present disclosure have been illustrated. However, the present disclosure can be implemented in various manners, and thus should not be construed to be limited to the embodiments disclosed herein.

As mentioned in the backgiteration, more and more industries are beginning to apply AI to help to solve industry-specific problems. Such application involves a wide range of activities including medical diagnosis, electronic trading, robot control, and remote sensing, etc. AI has been used to develop and advance numerous fields and industries, including finance, healthcare, education, transportation, and more. An example of an application of AI is virtual diagnosis which typically is a conversation-based inquiry and diagnosis service based on knowledge graph. A virtual diagnosis service may be a disease diagnosis service in healthcare industry, or a troubleshooting service, etc. However, existing approaches of virtual diagnosis services do not provide any feedback of the diagnosis process which may discourage the use of the services.

Embodiments of the invention can be deployed on cloud computer systems which will be described in the following. It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 1:
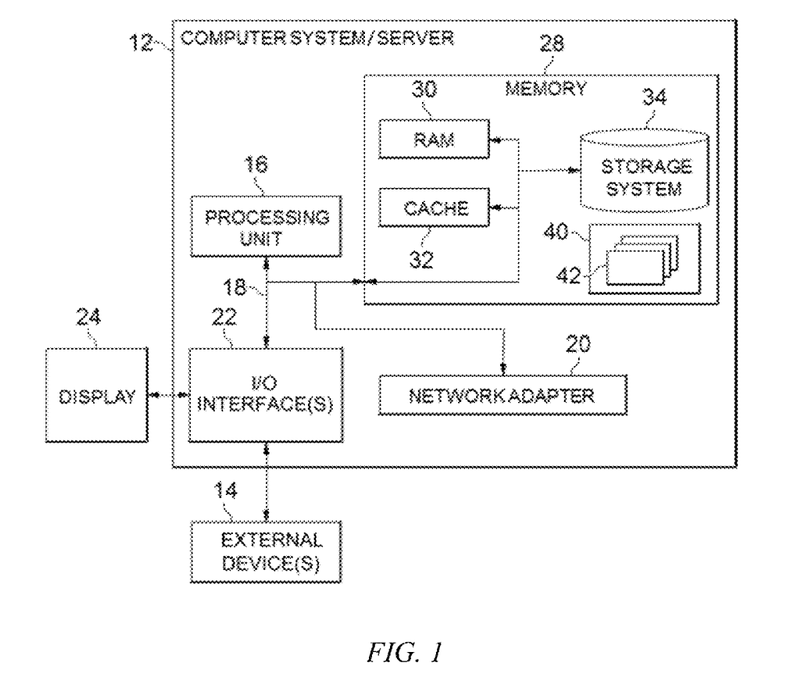
FIG. 1 depicts a cloud computing node according to an embodiment of the present invention.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12 or a portable electronic device such as a communication device, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
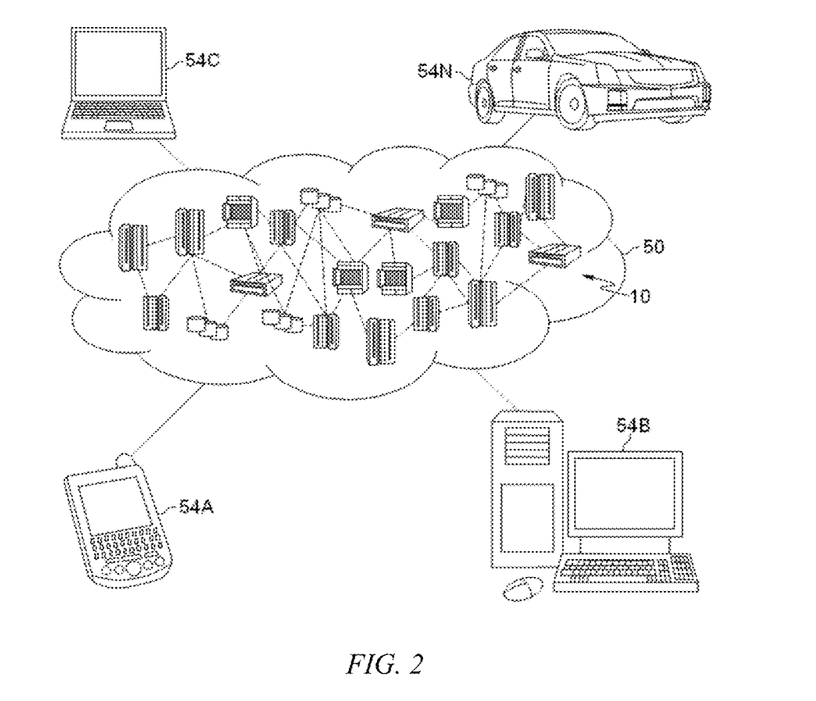
FIG. 2 depicts a cloud computing environment according to an embodiment of the present invention.

Referring now to FIG. 2, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
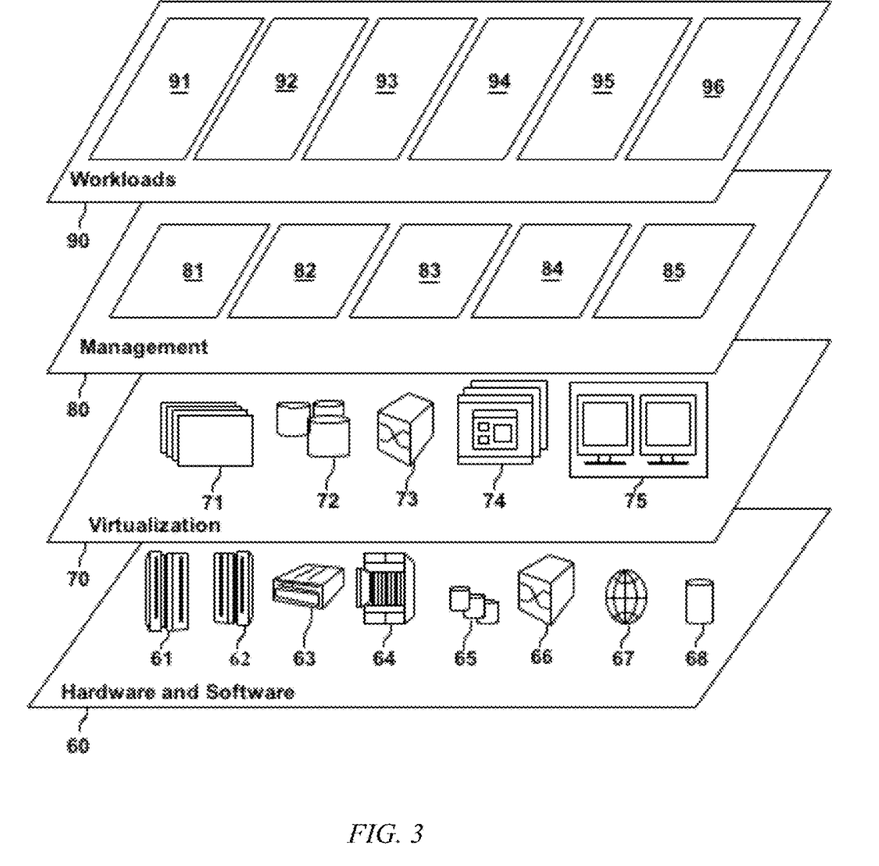
FIG. 3 depicts abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and progress evaluation 96 according to embodiments of the invention.

As afore-mentioned, embodiments of the invention are targeting the problem that no feedback is provided for a diagnosis process in virtual diagnosis services nowadays. Embodiments of the invention provide feedback for a diagnosis process. In the following, embodiments of the present invention will be discussed in detail with a disease diagnosis service as the virtual diagnosis service, however, it should be pointed out that embodiments of the invention can also be applied to other types of knowledge graph-based virtual diagnosis services. The examples should not adversely limit the scope of the invention.

Figure 4:
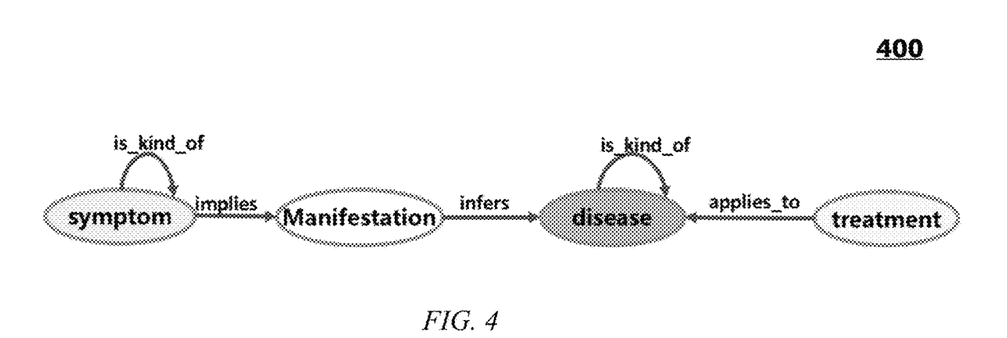
FIG. 4 depicts an illustration of a meta model 400 of medical knowledge graph.

Generally speaking, knowledge graphs are large networks of entities, their semantic types, properties, and relationships between entities. A knowledge graph can acquire and integrate information into an ontology and apply a reasoner to derive new knowledge. A knowledge graph mainly describes real world entities and their interrelations, organized in a graph, which defines possible classes and relations of entities in a schema and allows for potentially interrelating arbitrary entities with each other and covers various topical domains. Medical knowledge graphs are a type of knowledge graph used in the healthcare domain. FIG. 4 depicts an illustration of a meta model 400 of medical knowledge graphs. As shown in FIG. 4, a typical medical knowledge graph can comprise multiple parts and their relationships as shown in FIG. 4, wherein the terms "symptom," "manifestation," "disease" and "treatment" refer to different types of nodes in the graph, and "is_kind_of," "implies," "infers," and "applies_to" refer to different relationships between nodes in the graph. In some cases, a "disease" type of nodes in medical knowledge graphs can also be referred as a "root cause" type of nodes in general. It should be pointed out that the meta model 400 of FIG. 4 is merely an example of a simplified illustration of a medical knowledge graph. Medical knowledge graphs used in real word can adopt different models other than the model 400 shown in FIG. 4.

Figure 5:
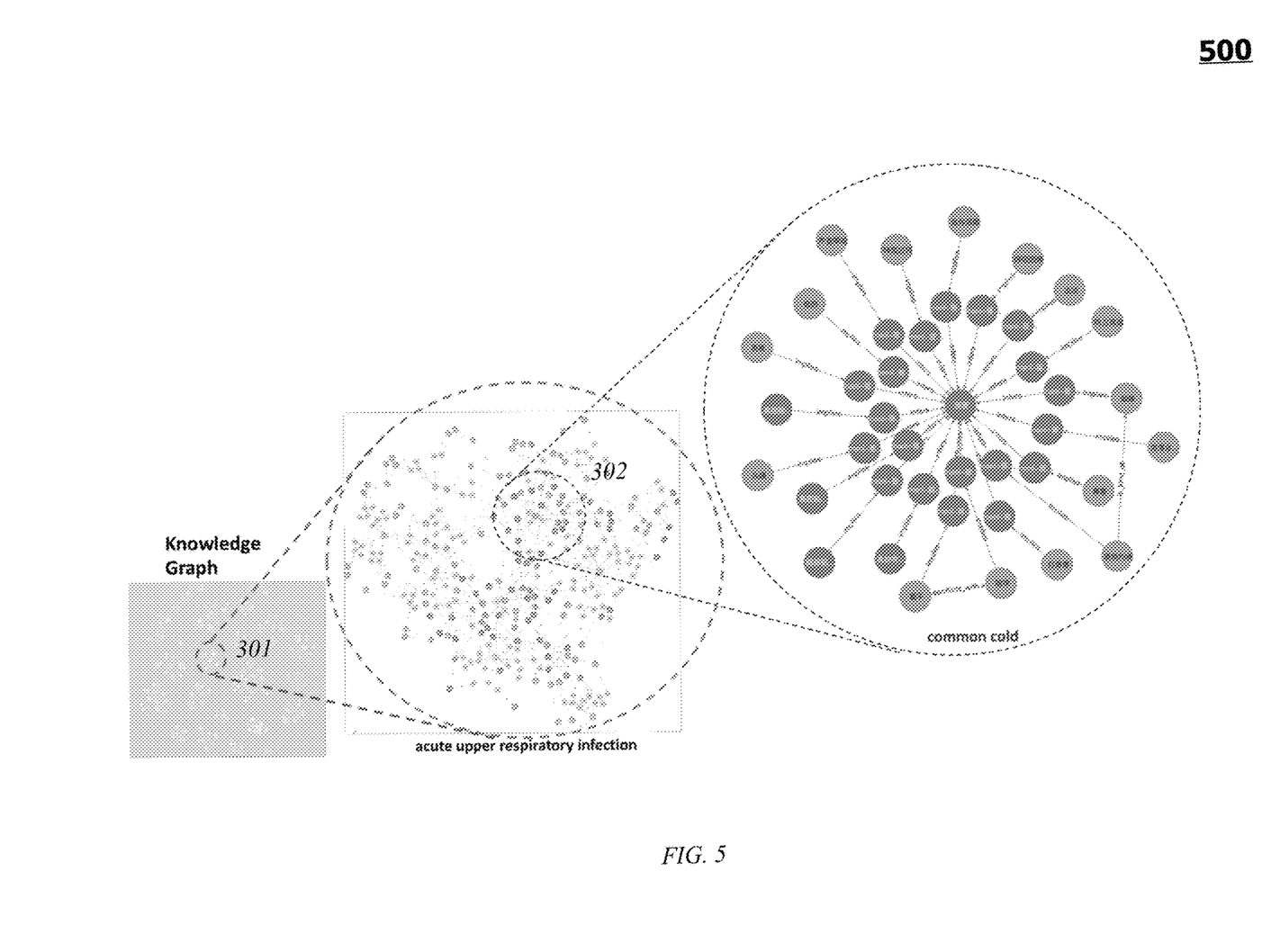
FIG. 5 depicts an overview of an example medical knowledge graph and its sub-graphs 500.

Referring now to FIG. 5, an overview of an example medical knowledge graph and some of its sub-graphs 500 is shown. In FIG. 5, a general medical knowledge graph is shown in the left of FIG. 5 with a circle 301 selected. Due to the complexity and large size of the graph, details cannot be seen clearly. An enlarged view of the selected circle 301 is shown in the middle of FIG. 5, which is a sub-graph of a type of disease (the "disease" type node in FIG. 4) named "acute upper respiratory infection". Due to the complexity and large size of the sub-graph, details cannot be seen clearly either. In the right of FIG. 5 is an enlarged view of a type of disease (circle 302, also the "disease" type node in FIG. 4, e.g. shown as the center node in the sub-graph) named "common cold". Due to the complexity and large size of the sub-graph, details cannot be seen clearly either.

Figure 6:
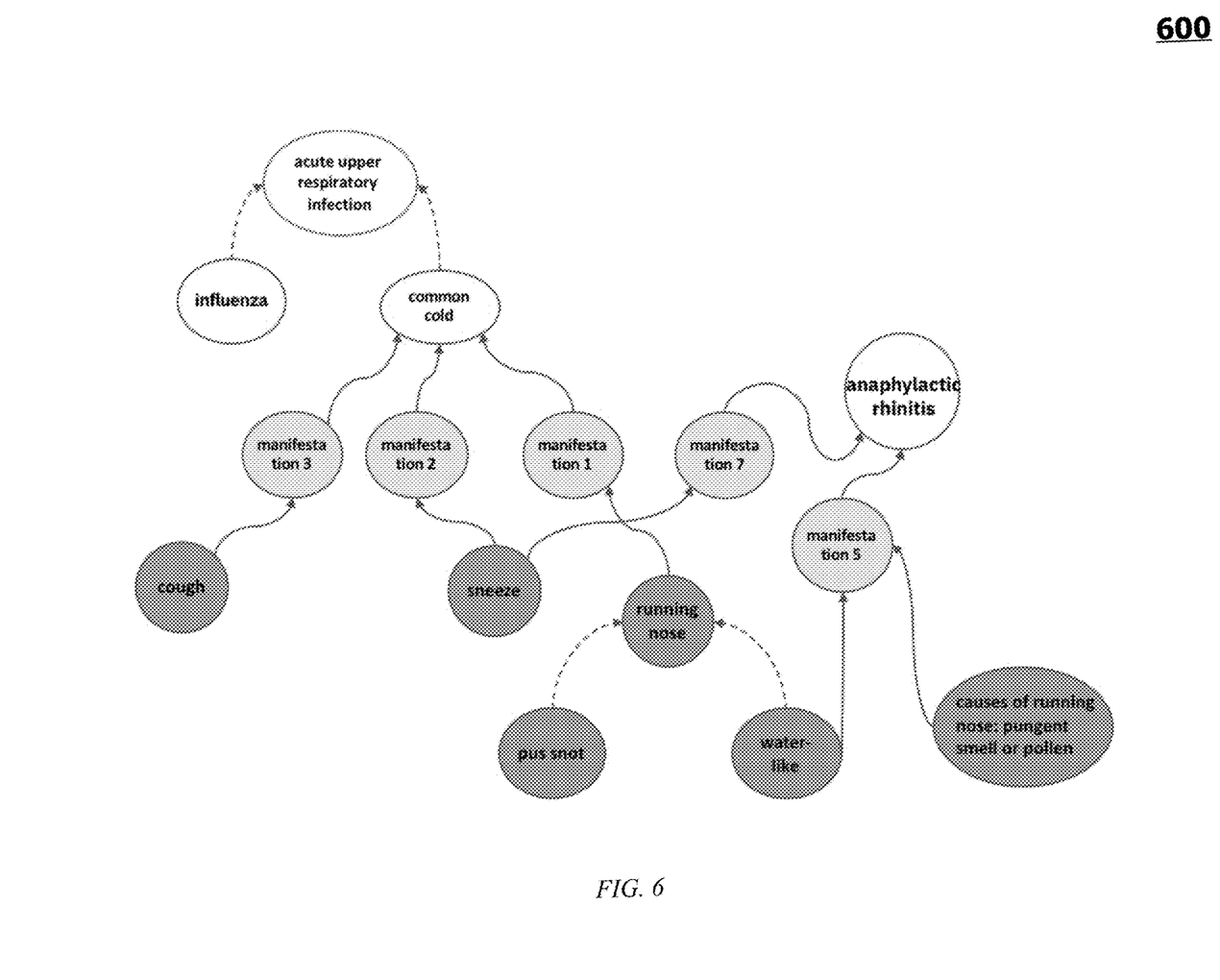
FIG. 6 depicts a simplified detailed view of an example sub-graph 600 which may be utilized by embodiments of the present invention.

In FIG. 6, a simplified detailed view of an example sub-graph 600 which can be utilized by embodiments of the present invention is depicted. In FIG. 6, for the purpose of simplified illustration, only "symptom" type nodes and "disease" type nodes are shown with specific values, e.g. "cough", "pus snot", and "influenza", "common cold", "manifestation" type nodes are merely shown with general description as "manifestation 3", "manifestation 2", "manifestation 1" and "manifestation 7". Specific values of relationships between nodes, as well as "treatment" type nodes are also omitted. As both knowledge graph and medical knowledge graph are known by those skilled in the arts in some embodiments, thus they will not be discussed in detail for the purpose of simplified illustration.

It should be pointed out, although the illustration of knowledge graphs of FIG. 4 to FIG. 6 are using medical knowledge graphs as examples, embodiments of the invention can also be applied to other types of knowledge graphs with similar model as shown in FIG. 4, e.g. knowledge graphs of a troubleshooting service with "symptom", "manifestation" and "treatment" types of nodes are the same and "root cause" substitutes "disease" type of nodes. The illustration of FIG. 4 to FIG. 6 is merely an example and should not adversely limit the scope of the invention. Also, as afore-mentioned, embodiments of the invention will be described with a disease diagnosis service as the virtual diagnosis service, embodiments of the invention can also be applied to other types of knowledge graph-based virtual diagnosis services. The examples should not adversely limit the scope of the invention.

Figure 7:
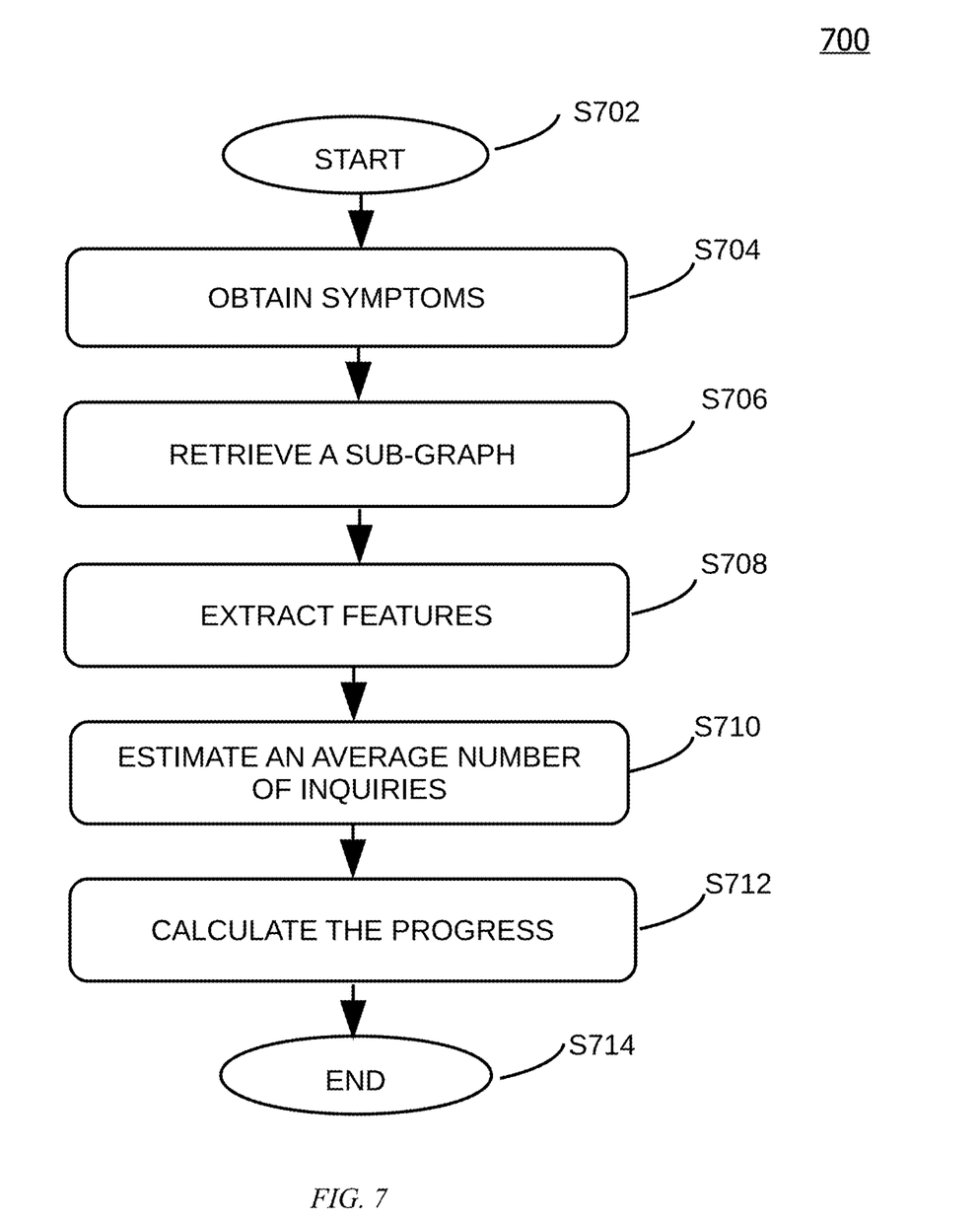
FIG. 7 depicts a flowchart of an example method 700 for evaluating a progress of a diagnosis process according to an embodiment of the present invention.

Referring now to FIG. 7, a flowchart of an example method 700 for evaluating a progress of a diagnosis process according to an embodiment of the present invention is shown. The method 700 starts at step S702. Then at step S704, a list of symptoms can be obtained, e.g. by a virtual diagnosis service. According to an embodiment of the invention, the list of symptoms can be obtained based on inputs of the virtual diagnosis service received from a user. The inputs can be at least one inquiry in the form of natural language which describes symptoms of the user, e.g., "I have been feeling headache for the past three days.", or simply describes the symptoms per se, e.g. "headache". Upon receiving the inputs from the user, natural language processing can be performed to identify name entities. The identified name entities can further be sent to a symptom name entity database where whether the identified name entities are corresponding to certain symptoms are determined. This can be done by simply querying the database with the identified name entities as keywords. If it is determined that an identified name entity is a symptom, it will be put into the list.

Responsive to the obtaining of the list of symptoms, the method 700 proceeds to step S706 where a sub-graph associated with the list of symptoms can be retrieved from a knowledge graph. The retrieval of the sub-graph can simply be implemented by querying the knowledge graph with the list of symptoms as keywords. The structure of knowledge graphs has already enabled such kind of query. For example, nodes in the knowledge graph that have the values matching the keywords can be firstly retrieved as start nodes, then edges connecting start nodes and next level nodes can then be retrieved, until a "disease" type node is reached. The retrieved sub-graph can comprise one or more nodes have the values matching the keywords as start nodes ("symptom" type nodes), a "disease" type node as end nodes and all paths from start nodes to end nodes. It should be pointed out that what kind of nodes will function as start nodes and what kind of nodes will function as end nodes in the sub-graph is subject to the service type, for example, if the service is a treatment service, and the user wants to know the treatment to a common cold, a node with the value "common cold" ("disease" type nodes) can function as start nodes, and one or more nodes connected to start nodes via edges with treatments to common code as its value ("treatment" type nodes) can function as end nodes. Then, the sub-graph can comprise a "disease" type node as start nodes, one or more "treatment" type nodes as end nodes and all paths from start nodes to end nodes. It should also be pointed out that the retrieval of sub-graphs associated with a keyword can adopt any existing technologies and will not be discussed in detail herein in order not to obscure embodiments of the invention.

Then at step S708, a list of features can be extracted from the retrieved sub-graph. In the example that the knowledge graph is a medical knowledge graph, the list of features can comprise at least one of the following: the number of symptoms in the sub-graph occurred in inquiries; the number of symptoms in the sub-graph not occurred in inquiries; the number of nodes in the sub-graph; the number of links in the sub-graph; the number of symptoms in the sub-graph; the average out-degree for symptoms in the sub-graph; the average in-degree for symptoms in the sub-graph; the number of diseases in the sub-graph; the average out-degree for diseases in the sub-graph; or the average in-degree for diseases in the sub-graph, etc. It should be pointed out the above list is not a thorough list, also more or less features can be extracted from the retrieved sub-graph. It should also be noted, for knowledge graphs of a trouble shooting system, "disease" should be "root cause".

With the list of features extracted, the method 700 proceeds to step S710 where an average number of inquiries can be estimated based on the extracted list of features. According to an embodiment of the invention, the extracted list of features is fed to a regression model trained beforehand. The input of the regression model is a list of features (for example the list of features extracted at step S708) and the output of the regression model is an estimated average number of inquiries associated with the list of features. The training of the regression model will be discussed later with reference to FIG. 8 hereinafter.

Then at step S712, the progress of the diagnosis process is calculated. According to an embodiment of the invention, a current number of inquiries can be firstly obtained, and the progress of the diagnosis process can be calculated by dividing the current number of inquiries by the estimated average number of inquiries. The current number of inquiries refers to the total number of inquiries from the beginning of the diagnosis process (i.e. the first inquiry) till the current inquiry. Then at step S714, the method 700 ends. Additionally, the progress can be provided to the user of the diagnosis service in a manner that the user can visually be aware of, e.g. a progress bar.

According to an embodiment of the invention, for each (or, in some embodiments, one or more) iteration of inquiries, the obtaining of a list of symptoms, the retrieval of a sub-graph, the extraction of a list of features, the estimation of an average number of inquiries and the calculation of the progress can be performed recursively so that the progress of the diagnosis process can be calculated dynamically with the inputs of the user so that the user can be aware of the progress dynamically.

Figure 8:
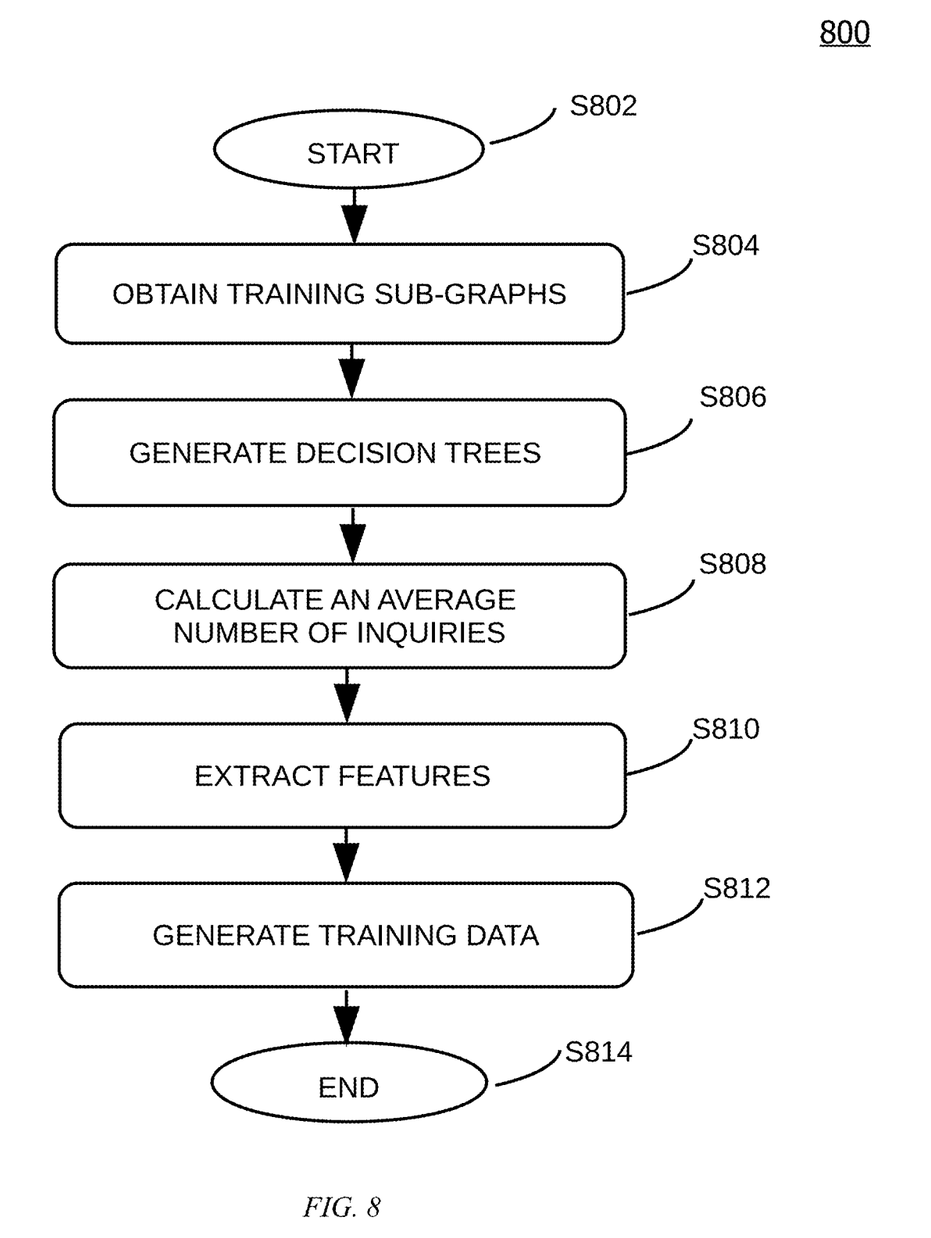
FIG. 8 depicts a flowchart of an example method 800 for training a regression model for the evaluation of a progress of a diagnosis process according to an embodiment of the present invention.

Referring now to FIG. 8, a flowchart of an example method 800 for training a regression model for the evaluation of a progress of a diagnosis process according to an embodiment of the present invention is depicted. The method 800 starts at step S802. Then at step S804, a plurality of training sub-graphs associated with a list of symptoms can be obtained. A training sub-graph can comprise one or more "symptom" type nodes as start nodes, one or more "disease" type nodes as end nodes, and all paths from start nodes to end nodes. It should be pointed out that what kind of nodes function as start nodes and what kind of nodes function as end nodes in the training sub-graph is subject to the service type, for example, if the service is a treatment service, "disease" type nodes can function as start nodes and "treatment" type nodes can function as end nodes. The sub-graph can comprise one or more "disease" type nodes as start nodes, one or more "treatment" type nodes as end nodes and all paths from start nodes to end nodes. Then at step S806, for the plurality of training sub-graphs, a corresponding decision tree can be generated respectively for each (or, in some embodiments, one or more) of the training sub-graphs. According to an embodiment of the invention, the respective decision tree can be generated in a manner to maximize the information gain, also known as Kullback-Leibler divergence. Then at step S808, a corresponding average number of inquiries associated with the list of symptoms can be calculated respectively for each (or, in some embodiments, one or more) of the training sub-graphs based on the generated corresponding decision tree, wherein an average number of inquiries associated with a list of symptoms refers to the average number of edges of all paths from a start node to an end node associated with the list of symptoms. At step S810, a corresponding list of features can be extracted respectively for each (or, in some embodiments, one or more) of the sub-graphs. Then with the extracted lists of features, the calculated average numbers of inquiries corresponding to each (or, in some embodiments, one or more) of the training sub-graphs, training data of the regression model can be generated at step S812. Then the regression model is trained with the generated training data. The regression model can be expressed as $Y \approx f(X, \beta)$, wherein X is the set of independent variables (typically a vector, e.g. the extracted features in the disclosure), Y is the dependent variable (average number of inquiries in the disclosure) and $\beta$ is an unknown parameter which needs to be trained. The training of the regression model can utilize any existing technologies, e.g., with a neural network. After a successful training of the neural network, $\beta$ is determined, which means the regression model is determined. The input of the trained regression model is a list of features and the output of the trained regression model is an estimated average number of inquiries. With the trained regression model, there is no need to generate decision trees for a sub-graph in runtime. Only a list of features needs to be extracted and fed to the regression model to get an estimated average number of inquiries. The use of the trained regression model significantly reduces computing costs, and thus can provide a timely feedback during runtime to the user of the virtual diagnosis service.

It should be noted that the processing of a progress evaluation of a diagnosis process (or achieved by the progress evaluation of a diagnosis process) according to embodiments of this disclosure could be implemented by computer system/server 12 of FIG. 1.

The present invention can be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user"s computer, partly on the user"s computer, as a stand-alone software package, partly on the user"s computer and partly on a remote computer or entirely on the remote computer or server. In the latter scenario, the remote computer may be connected to the user"s computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, comprising:
   obtaining, by a device operatively coupled to one or more processing units, a list of one or more symptoms;
   retrieving, by the device, a sub-graph associated with the list of the one or more symptoms from a knowledge graph;
   extracting, by the device, a list of one or more features from the retrieved sub-graph, wherein the list of the one or more features comprises an average out-degree for the one or more symptoms in the sub-graph or an average in-degree for the one or more symptoms in the sub-graph;
   estimating, by the device, an average number of inquiries based on the extracted list of one or more features, wherein the estimating comprises processing the extracted list of the one or more features via a trained regression model employing a neural network, wherein an input to the trained regression model is the list of the one or more features and an output of the regression model is the estimated average number of inquiries associated with the one or more features; and
   calculating, by the device, the progress of the diagnosis process based on the estimated average number of natural language inquiries to provide a virtual diagnosis service, wherein the use of the trained regression model reduces computing costs for the device and enables feedback during runtime of the virtual diagnosis service.

2. The computer-implemented method of claim 1, wherein the estimation of the average number of inquiries based on the extracted list of the one or more features further comprises:
   obtaining, by the device, the estimated average number of inquiries.

3. The computer-implemented method of claim 2, wherein the trained regression model is trained by:
   generating, by the device, corresponding decision trees respectively for a plurality of training sub-graphs;

calculating, by the device, corresponding average numbers of inquiries respectively for the plurality of training sub-graphs based on the corresponding generated decision trees;
extracting, by the device, corresponding lists of one or more features respectively for the plurality of training sub-graphs; and
generating, by the device, training data of the regression model with the extracted lists of the one or more features and the corresponding calculated average numbers of inquiries.

4. The computer-implemented method of claim 1, wherein the calculation of the progress of the diagnosis process comprises:
obtaining, by the device, a current number of inquiries, wherein the current number of inquiries refers to a total number of inquiries from a beginning of the diagnosis process until a current inquiry; and
dividing, by the device, the current number of inquiries by the estimated average number of inquiries.

5. The computer-implemented method of claim 1, wherein the obtaining, retrieving, extracting, estimating and calculating are performed recursively for each iteration of inquiries.

6. The computer-implemented method of claim 1, wherein the obtaining of the list of the one or more symptom comprises:
receiving, by the device, at least one inquiry from a user; and
performing, by the device, natural language processing on the received at least one inquiry.

7. The computer-implemented method of claim 1, wherein the list of extracted one or more features comprises at least one of the following: the number of symptoms in the sub-graph occurred in inquires; the number of symptoms in the sub-graph not occurred in inquires; the number of nodes in the sub-graph; the number of links in the sub-graph; the number of symptoms in the sub-graph; the number of root causes in the sub-graph; the average out-degree for root causes in the sub-graph; or the average in-degree for root causes in the sub-graph.

8. A computer program product facilitating evaluation of the progress of a diagnosis process, the computer program product comprising a computer readable storage medium having program instructions embodied therewith, the program instructions executable by a processor to cause the processor to:
obtain a list of one or more symptoms;
retrieve a sub-graph associated with the list of one of the more symptoms from a knowledge graph;
extract a list of one or more features from the retrieved sub-graph, wherein the list of the one or more features comprises an average out-degree for the one or more symptoms in the sub-graph or an average in-degree for the one or more symptoms in the sub-graph;
estimate an average number of inquiries based on the extracted list of one or more features, wherein the estimation comprises processing the extracted list of the one or more features via a trained regression model employing neural networks, wherein an input to the trained regression model is a vector comprising the list of the one or more features and an output of the regression model is the estimated average number of inquiries associated with the one or more features, wherein the processing via the trained regression model reduces computing costs of the processor and reduces the time to provide feedback during runtime of the virtual diagnosis service, and wherein the average number of inquiries associated with a list of the one or more symptoms refers to an average number of edges of all paths from a start node to an end node associated with the list of the one or more symptoms; and
calculate the progress of the diagnosis process based on the estimated average number of inquiries to provide a virtual diagnosis service.

9. The computer program product of claim 8, wherein estimation of the average number of inquiries based on the extracted list of the one or more feature further comprises:
obtaining the estimated average number of inquiries.

10. The computer program product of claim 9, wherein the regression model is trained by:
generation of corresponding decision trees respectively for a plurality of training sub-graphs;
calculation of corresponding average numbers of inquiries respectively for the plurality of training sub-graphs based on the corresponding generated decision trees;
extraction of corresponding lists of the one or more features respectively for the plurality of training sub-graphs; and
generation of training data of the regression model with the extracted lists of features and the corresponding calculated average numbers of inquiries.

11. The computer program product of claim 8, wherein the calculation of the progress of the diagnosis process comprises:
obtaining a current number of inquiries;
dividing the current number of inquiries by the estimated average number of inquiries.

12. The computer program product of claim 8, wherein the obtaining, retrieving, extracting, estimating and calculating are performed recursively for at least one iteration of inquiries.

13. The computer program product of claim 8, wherein the obtaining of the list of one or more symptoms comprises:
receiving at least one inquiry from a user; and
performing natural language processing on the received at least one inquiry.

14. The computer program product of claim 8, wherein the list of extracted one or more features further comprises at least one of the following: the number of symptoms in the sub-graph occurred in inquiries; the number of symptoms in the sub-graph not occurred in inquiries; the number of nodes of the sub-graph; the number of links of the sub-graph; the number of symptoms in the sub-graph; the number of root causes in the sub-graph; the average out-degree for root causes in the sub-graph; or the average in-degree for root causes in the sub-graph.

15. A computer system, comprising:
a memory that stores computer executable components; and
a processing unit that executes the computer executable components stored in the memory, wherein the computer executable components comprise:
at least one computer-executable component that:
obtains a list of one or more symptoms;
retrieves a sub-graph associated with the list of symptom from a knowledge graph;
extracts a list of one or more features from the retrieved sub-graph, wherein the list of the one or more features comprises an average out-degree for the one or more symptoms in the sub-graph or an average in-degree for the one or more symptoms in the sub-graph;
estimates an average number of inquiries based on the extracted list of one or more features, wherein the estimation comprises a feeding of the extracted list of the one or more features to a trained regression model, wherein an input to the trained regression model is the list of the one or more features and an output of the regression model is the estimated average number of inquiries associated with the one or more features;

calculates the progress of the diagnosis process based on the estimated average number of inquiries to provide a virtual diagnosis service, wherein the use of the trained regression model reduces computing costs for the device and enables timely feedback during runtime of the virtual diagnosis service; and generates and displays, via a user interface operatively coupled to the system, a visual progress bar indicative of a progress, at a defined time, of the virtual diagnosis service, wherein the calculation of the progress is performed recursively so that the progress of the diagnosis process is calculated dynamically and the generation and the display is updated dynamically.

16. The system of claim 15, wherein the estimation of the average number of inquiries based on the extracted list of the one or more features comprises:

feeding the extracted list of the one or more features to a regression model, wherein the input of the regression model is a list of the one or more features and the output is an estimated average number of inquiries associated with the list of the one or more features; and obtaining the estimated average number of inquiries.

17. The system of claim 16, wherein the regression model is trained by:

generation of corresponding decision trees respectively for a plurality of training sub-graphs;

calculation of corresponding average numbers of inquiries respectively for the plurality of training sub-graphs based on the corresponding generated decision tree;

extraction of corresponding lists of features respectively for the plurality of training sub-graphs; and generation of training data of the regression model with the extracted lists of features and the corresponding calculated average numbers of inquiries.

18. The system of claim 15, wherein the calculation of the progress of the diagnosis process comprises:

obtaining a current number of inquiries;

dividing the current number of inquiries by the estimated average number of inquiries.

19. The system of claim 15, wherein the obtaining of the list of one or more symptoms comprises:

receiving at least one inquiry from a user; and performing natural language processing on the received at least one inquiry.

20. The system of claim 15, wherein the list of extract one or more features further comprises at least one of the following: the number of symptoms in the sub-graph occurred in inquiries; the number of symptoms in the sub-graph not occurred in inquiries; the number of nodes of the sub-graph; the number of links of the sub-graph; the number of symptoms in the sub-graph; the number of root causes in the sub-graph; the average out-degree for root causes in the sub-graph; or the average in-degree for root causes in the sub-graph.

* * * * *